United States Patent [19]

Hasegawa

[11] Patent Number: 5,371,202
[45] Date of Patent: Dec. 6, 1994

[54] PROCESSES OF PREPARING SIALOGLYCOSYL COMPOUNDS

[75] Inventor: Akira Hasegawa, Gifu, Japan

[73] Assignee: The Nisshin Oil Mills, Ltd., Tokyo, Japan

[21] Appl. No.: 833,794

[22] Filed: Feb. 12, 1992

[30] Foreign Application Priority Data

Feb. 28, 1991 [JP] Japan .................................. 3-055658

[51] Int. Cl.$^5$ .......................... C07H 5/10; C07H 1/00; C07H 23/00
[52] U.S. Cl. ..................................... 536/17.5; 536/4.1; 536/17.2; 536/18.5
[58] Field of Search ....................... 536/4.1, 17.5, 18.2, 536/18.5, 53, 54, 55.3, 122, 124, 1.1

[56] References Cited

U.S. PATENT DOCUMENTS

| 4,871,837 | 10/1989 | Magnusson et al. | 536/4.1 |
| 4,935,506 | 6/1990 | Goto et al. | 536/4.1 |
| 5,101,026 | 3/1992 | Ogawa et al. | 536/53 |
| 5,138,044 | 8/1992 | Dasgupta | 536/4.1 |

FOREIGN PATENT DOCUMENTS

| 1290689 | 11/1989 | Japan . |
| 278694 | 3/1990 | Japan . |
| 3101691 | 4/1991 | Japan . |

OTHER PUBLICATIONS

Science of Life, vol. 28, No. 4, pp. 332–339, 1987, Y. Suzuki.
Experimental Medicine, vol. 6, No. 11, pp. 12(1028)–13(1029), 1988, Y. Nagai.
J. Biochem., vol. 94, No. 1, pp. 303–306, 1983, S. Tsuji, et al., "GQ1b, A Bioactive Ganglioside that Exhibits Novel Nerve Growth Factor (NGF)–Like Activities in the Two Neuroblastoma Cell Lines".
Science, vol. 7, pp. 71–83, 1986, S. Hakomori.
Clinical Pathology, vol. 34, No. 11, pp. 1247–1264, 1986, R. Kannagi.
Chemistry and Applications of Glycoconjugates, pp. 80–104, 1989, ed. by H. Ogura.
Carbohydrate Research, vol. 188(1989), Elsevier Science Publishers B.V., Amsterdam, NL, pp. 71–80, T. Murase, et al., "A Facile Regio- and Stereo–Selective Synthesis of Ganglioside GM$_3$".
J. Carbohydrate Chemistry, 7(2), 1988, pp. 453–486, E. Kirchner, et al., "Studies of the Glycosylation of N–Acetylneuraminic Acid".
Veeneman et al., *Tetrahydron Letters*, vol. 31(9), pp. 1331–1334, (1990).
Konradsson et al., *Tetrahedron Letters*, vol. 31(30), pp. 4313–4316, (1990).
Murase et al., *Carbohydrate Research*, vol. 188, pp. 71–80, (1989).
Kirchner et al., *J. Carbohydrate Chemistry*, vol. 7(2), pp. 453–486 (1988).
Ito et al.; Chemical Abstracts, 112:36277r (1990).
Kiso et al.; Chemical Abstracts, 112:153763g (1990).
Knapp et al.; Tet. Lett. 32(30):3627–3630 (1991).

*Primary Examiner*—John W. Hollins
*Assistant Examiner*—Howard C. Lee
*Attorney, Agent, or Firm*—Oblon, Spivak, McClelland, Maier & Neustadt

[57] ABSTRACT

An improved process for the preparation of O-glycosyl compounds of sialic acid, which are useful as intermediates in the synthesis of sialoconjugated glycosides. This process comprises effecting condensation reaction between thioglycosides of sialic acid and sugar derivatives in the presence of N-iodosuccinimide and trifluoromethanesulfonic acid. O-glycosyl compounds of sialic acid are prepared in high resio- and stereo-selectivity and in high yields.

9 Claims, No Drawings

PROCESSES OF PREPARING SIALOGLYCOSYL COMPOUNDS

FIELD OF THE INVENTION

This invention relates to processes of preparing O-glycosyl compounds of sialic acid. More particularly, the invention relates to methods of glycosylating sialic acid stereoselectively using thioglycosides of sialic acid.

BACKGROUND OF THE INVENTION

In the organic synthesis of sialoconjugated glycosides, the glycosylation of sialic acid, especially the condensation with a secondary hydroxyl group has been the most difficult reaction. This may be attributable to the facts that a steric hindrance at the anomeric position of sialic acid is increased by a quaternary carbon at its position; 2,3-dehydro form is easy to produce in the condensation reaction by a deoxy at the C-3 position adjacent to the anomeric position; the participation of neighboring groups cannot be utilized in the control of stereochemistry at the anomeric position and a thermodynamically stable configuration is a non-natural β-configuration. Various approaches have been used to solve those problems. An approach is to use the α-SMe form of sialic. acid as a sialic acid donor, α-galactose or α-lactose as a sugar acceptor and dimethyl(methylthio)-sulfoniumtriflate as a condensing agent for the glycosylation to synthesize the sialyllactose (α-form) in a yield of 47% (T. Murase et al, Carbohydr. Res., 188, 71 (1989)). Another approach is to use the α-SPh form of sialic acid as a sialic acid donor, condensing it with d primary hydroxyl group of the sugar in the presence of PhHgOTf (Tf=trifluoromethanesulfonyl) catalyst to synthesize α-glycoside in a yield of 24% (E. Kirchner et al, J. Carbohydr. Chem., 7, 453 (1988)). However, many problems still remain in the synthesis of sialoconjugated glycosides, since saccharide chains contained in conjugated glycosides are of high diversity.

SUMMARY OF THE INVENTION

An object of the invention is to provide a process of preparing O-glycosyl compounds of sialic acid in high regio- and stereo-selectivity, in high yields and in an economical way.

Another object of the invention is to provide an efficient glycosylation of sialic acid using a suitably protected sugar donor and a suitably protected sugar acceptor.

In accordance with the present invention, there is provided a process of preparing O-glycosyl compounds of sialic acid by reacting thioglycosides of sialic acid with sugar derivatives in the presence of N-iodosuccinimide and trifluoromethanesulfonic acid.

DETAILED DESCRIPTION OF THE INVENTION

The present invention is characterized by employing thioglycosides of sialic acid as a sugar donor and galactose or lactose derivatives containing the lowest protected hydroxyl groups as a sugar acceptor and further by conducting the condensation reaction in the presence of N-iodosuccinimide (NIS) and trifluoromethanesulfonic acid (TfOH).

The sialoglycosyl compounds can be prepared as shown in the following schemes 1 and 2 which illustrate preferred embodiments of the present invention.

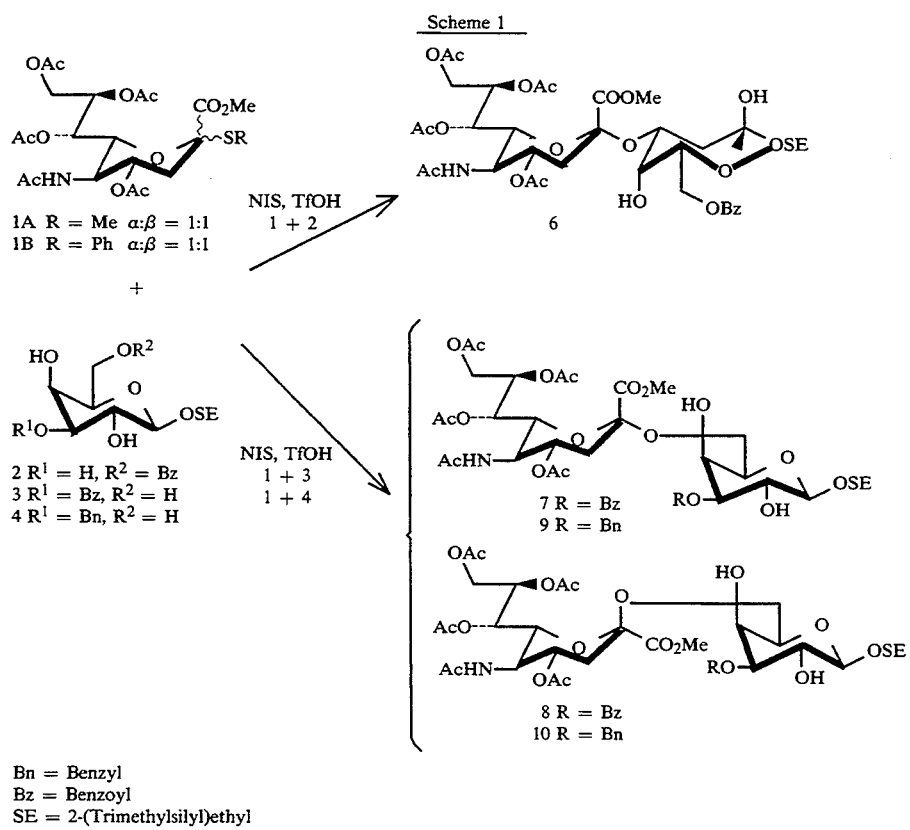

Scheme 1

Bn = Benzyl
Bz = Benzoyl
SE = 2-(Trimethylsilyl)ethyl

Scheme 2

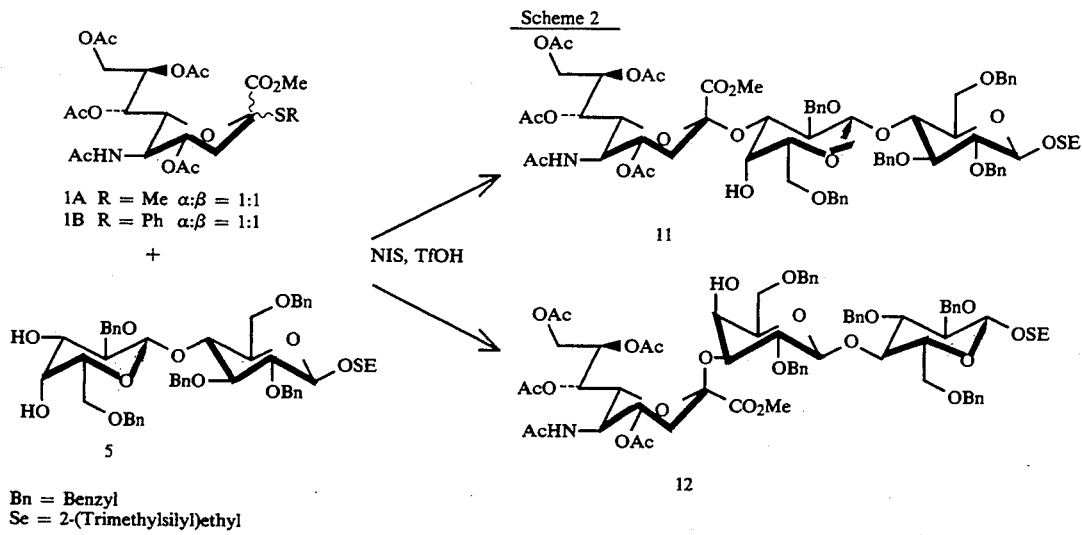

Bn = Benzyl
Se = 2-(Trimethylsilyl)ethyl

Examples of the sugar donor include methyl(methyl 5-acetamido- 4,7,8,9-tetra-O-acetyl-3,5-dideoxy-2-thio-D-glycero-D-galacto-2-nonulopyranosid)onate (Compound 1A, SMe form of sialic acid) and methyl(phenyl 5-acetamido-4,7,8,9-tetra-O-acetyl-3,5-dideoxy-2-thio-D-glycero-D-galacto-2-nonulopyranosid)onate (Compound 1B, SPh form of sialic acid ), as shown in schemes 1 and 2.

Examples of the sugar acceptor include galactose derivatives such as 2-(trimethylsilyl)ethyl 6-O-benzoyl-β-D-galactopyranoside (Compound 2), 2-(trimethylsilyl)ethyl 3-O-benzoyl-β-D-galactopyranoside (Compound 3) and 2-trimethylsilyl)ethyl 3-O-benzyl-β-D-galactopyranoside (Compound 4), as shown in scheme 1, and lactose derivatives such as 2-(trimethylsilyl)ethyl (2,6-di-O-benzyl-β-D-galactopyranosyl)-(1→4)-2,3,6-tri-O-benzyl-β-D-glucopyranoside (Compound 5), as shown in scheme 1.

The O-glycosyl compounds prepared by the present processes include 2-(trimethylsilyl)ethyl O-(methyl 5-acetamido-4,7,8,9-tetra-O-acetyl-3,5-dideoxy-D-glycero-α-D-galacto-2-nonulopyranosylonate)-(2→3)-6-O-benzoyl-β-D-galactopyranoside (Compound 6), 2-(trimethylsilyl)ethyl O-(methyl 5-acetamido-4,7,8,9-tetra-O-acetyl-3,5-dideoxy-D-glycero-α-D-galacto-2-nonulopyranosylonate)-(2→6)-3-O-benzoyl-β-D-galactopyranoside (Compound 7), 2-(trimethylsilyl)ethyl O-(methyl 5-acetamido-4,7,8,9-tetra-O-acetyl-3,5-dideoxy-D-glycero-β-D-galacto-2-nonulopyranosylonate)-(2→6)-3-O-benzoyl-β-D-galactopyranoside (Compound 8), 2-(trimethylsilyl)ethyl O-(methyl 5-acetamido-4,7,8,9-tetra-O-acetyl-3,5-dideoxy-D-glycero-α-D-galacto-2-nonulopyranosylonate)-(2→6)-3-O-benzyl-β-D-galactopyranoside (Compound 9) and 2-trimethylsilyl)ethyl O-(methyl 5-acetamido-4,7,8,9-tetra-O-acetyl-3,5-dideoxy-D-glycero-β-D-galacto-2-nonulopyranosylonate )-(2→6)-3-O-benzyl-β-D-galactopyranoside (Compound 10), as shown in scheme 1 and further include 2-(trimethylsilyl)ethyl O-(methyl-5-acetamido-4,7,8,9-tetra-O-acetyl-3,5-dideoxy-D-glycero-α-D-galacto-2-nonulopyranosylonate)-(2→3)-(2,6-di-O-benzyl-β-D-galactopyranosyl)-(1→4)-2,3,6-tri-O-benzyl-β-D-glucopyranoside (Compound 11) and 2-(trimethylsilyl)ethyl O-(methyl 5-acetamido-4,7,8,9-tetra-O-acetyl-3,5-dideoxy-D-glycero-β-D-galacto-2-nonulopyranosylonate)-(2→3)-(2,6-di-O-benzyl-β-D-galactopyranosyl)-(1→4)-2,3,6-tri-O-benzyl-β-D-glucopyranoside (Compound 12), as shown in scheme 2.

In the practice of the invention, the sugar donor and the sugar acceptor are first dehydrated in an appropriate solvent and cooled. The dehydrated compounds are subjected to the condensation reaction in the presence of N-iodosuccinimide and trifluoromethanesulfonic acid.

Appropriate solvents are chosen depending on the desired products. By choice of the solvents, there can be prepared desired compounds different in the bond position and/or stereoisomerism. The solvents used in this invention can include any solvents conventionally used in the synthesis of sialoglycosyl compounds, including acetonitrile, dichloromethane, chloroform or the like. Acetonitrile is preferable for increasing the production ratio of α-form.

Preferably, the sugar acceptor is used in an amount of 0.5 to 1 mole per mole of the sugar donor, N-iodosuccinimide is used in an amount of 1 to 2 moles and trifluoromethanesulfonic acid is used in an amount of 0.1 to 0.2 mole per mole of the sugar donor, but not limiting thereto. Other known reagents such as a dehydrating agent may be used for the preparation of sialoglycosyl compounds.

The reaction is carried out at temperatures between −80° and −20° C., preferably at −40° C., so as not to adversely affect the sugar donor and the sugar acceptor. As an example of the reaction, scheme 1 shows 1+2→6; 1+3→7; 1+3→7+8; 1+4→9+10 and scheme 2 shows 1+5→11+12. After completion of the reaction, such after-treatment as addition of terminator, extraction of solvent, removal of solvent or the like may be performed in a conventional manner. If necessary, purification may be conducted by conventional means such as column chromatography.

The glycosyl compound (Compound 6) prepared from the reaction of Compounds 1 and 2 is a useful intermediate in the synthesis of sacchadride chain antigen, 2→3 sialyl Lc4. Compound 11 prepared from the reaction of Compounds 1 and 5 is a useful intermediate in the synthesis of ganglioside GM$_3$, GM$_2$ and GM$_1$.

The invention is further illustrated by the following examples.

EXAMPLE 1

2-(Trimethylsilyl)ethyl O-(methyl 5-acetamido-4,7,8,9-tetra-O-acetyl-3,5-dideoxy-D-glycero-α-D-galacto-2-nonulopyranosylonate)-(2→3)-6-O-benzoyl-β-D-galactopyranoside (Compound 6)

A) To a solution of Compound 1A (2.52 g, 4.42 mmol) and Compound 2 (1.0 g, 2.60 mmol) dissolved in acetonitrile (20 ml) was added Molecular Sieves 3A (5 g) and the solution was stirred at room temperature for 10 hrs. To the reaction solution cooled to −40° C. were added N-iodosuccinimide (1.0 g, 4.42 mmol) and further trifluoromethanesulfonic acid (45 μl, 0.44 mmol) and a mixture was stirred at −40° C. for 2 hrs. After a completion of the reaction was confirmed by thin layer chromatography, the reaction solution was neutralized with triethylamine, the molecular sieves was filtered off and the filtrate was washed well with dichloromethane. The filtrate and washings were combined and concentrated at 45° C. under reduced pressure. The resulting syrup was diluted with dichloromethane, washed with successive $Na_2S_2O_3$ and $H_2O$, dried over $Na_2SO_4$ and concentrated at 45° C. under reduced pressure. The resultant syrup was subjected to silica gel column chromatography (Wakogel; C-200) using 3/1 ethyl acetate/hexane as an eluting solvent to obtain Compound 6 (1.35 g, 60.5%) as a syrup.

B) To a solution of Compound 1B (7.74 g, 13.3 mmol) and Compound 2 (3.0 g, 7.8 mmol) dissolved in acetonitrile (60 ml) was added Molecular Sieves 3A (10 g) and the solution was stirred at room temperature for 10 hrs. To the reaction solution cooled to −40° C. were added N-iodosuccinimide (5.97 g, 26.5 mmol) and further trifluoromethanesulfonic acid (235 μl, 2.65 mmol) and a mixture was stirred at −40° C. for 2 hrs. After a completion of the reaction was confirmed by thin layer chromatography, the reaction solution was neutralized with triethylamine, the molecular sieves was filtered off and the filtrate was washed well with dichloromethane. The filtrate and washings were combined and concentrated at 45° C. under reduced pressure. The resulting syrup was diluted with dichloromethane, washed with successive $Na_2S_2O_3$ and $H_2O$, dried over $Na_2SO_4$ and concentrated at 45° C. under reduced pressure. The resultant syrup was subjected to silica gel column chromatography (Wakogel; C-200) using 3/1 ethyl acetate/hexane as an eluting solvent to obtain Compound 6 (3.6 g, 53.8%) as a syrup.

Compound 6: $^1H$ NMR(CDCl$_3$) Gal unit δ1.06 (m, 2H, MeSiCH$_2$CH$_2$O), 2.49 (d, 1H, OH), 2.70 (1H, OH), 4.46 (d, 1H, $J_{1,2}$=7.69 Hz, H-1), 4.50–4.65 (m, 2H, H-6), 7.27–8.06 (m, 5H, Bz); Neu 5Ac unit δ1.77 (S, 3H, AcN), 1.90–2.11 (4S, 12H, 4AcO), 2.72 (dd, 1H, $J_{3,4}$=4.5 Hz, H-3$_e$) 4.25 (dd, 1H, $J_{8,9}$=2.63 Hz, $J_{gem}$=12.6 Hz, H-9), 4.95 (m, 1H, H-4), 5.28 (d, 1H, J=9.6 Hz, NNAc) 5.32 (dd, 1H, $J_{6,7}$=2.9 Hz, $J_{7,8}$=10.3 Hz, H-7), 5.45 (m, 1H, H-8)

EXAMPLE 2

2-(Trimethylsilyl)ethyl O-(methyl 5-acetamido-4,7,8,9-tetra-O-acetyl-3,5-dideoxy-D-glycero-α-D-galacto-2-nonulopyranosylonate-(2→6)-3-O-benzoyl-β-D-galactopyranoside (Compound 7)

To a solution of Compound 3 (700 mg, 1.82 mmol) and Compound 1A (1.61 g, 3.09 mmol) dissolved in acetonitrile (15 ml) was added Molecular Sieves 3A (2.3 g) and the solution was stirred at room temperature for 5 hrs. To the solution cooled to −40° C. were added N-iodosuccinimide (1.39 g, 6.17 mmol) and further trifluoromethanesulfonic acid (54.7 μl, 0.62 mmol) and a mixture was stirred at the same temperature for 2 hrs. After a completion of the reaction was confirmed by thin layer chromatography, the reaction solution was neutralized with triethylamine, the molecular sieves was filtered off and the filtrate was concentrated under reduced pressure. The resulting syrup was extracted with chloroform, washed with successive $Na_2CO_3$, 2N-HCl and $Na_2S_2O_3$, dried over $Na_2SO_4$ and the solvent was distilled off. The resultant syrup was subjected to silica gel column chromatography (Wakogel; C-200) and Compound 7 (917 mg, 58.8%) was obtained from a fraction eluting with 70/1 $CH_2Cl_2$/MeOH.

EXAMPLE 3

2-(Trimethylsilyl)ethyl O-(methyl 5-acetamido-4,7,8,9-tetra-O-acetyl-3,5-dideoxy-D-glycero-α-D-galacto-2-nonulopyranosylonate)-(2→6)-3-O-benzoyl-β -D-galactopyranoside (Compound 7)

and 2-(Trimethylsilyl)ethyl O-(methyl 5-acetamido-4,7,8,9-tetra-O-acetyl-3,5-dideoxy-D-glycero-β-D-galacto-2-nonulopyranosylonate)-(2→6)-3-O-benzoyl-β-D-galactopyranoside) (Compound 8)

To a solution of Compound 3 (700 mg, 1.82 mmol) and Compound 1A (1.61 g, 3.09 mmol) dissolved in dichloromethane (15 ml) was added Molecular Sieves 3A (2.3 g). The reaction was carried out by a similar way as in Example 2. After a completion of the reaction was confirmed by thin layer chromatography, the molecular sieves was filtered off and the filtrate was extracted with chloroform, washed with successive $Na_2CO_3$ and $Na_2S_2O_3$, dried over $Na_2SO_4$ and the solvent was distilled off. The resulting syrup was subjected to silica gel column chromatography (Wakogel; C-200) and a syrup Compound 7 (762 mg, 48.8%) and Compound 8 (388 mg, 24.8% ) were obtained from a fraction eluting with 70/1 $CH_2Cl_2$/MeOH.

EXAMPLE 4

2-(Trimethylsilyl)ethyl O-(methyl 5-acetamido-4,7,8,9-tetra-O-acetyl-3,5-dideoxy-D-glycero-α-D-galacto-2-nonulopyranosylonate)-(2→6)-3-O-benzyl-β-D-galactopyranoside (Compound 9)

and 2-(Trimethylsilyl)ethyl O-(methyl 5-acetamido-4,7,8,9-tetra-O-acetyl-3,5-dideoxy-D-glycero-β-D-galacto-2-nonulopyranosylonate)-(2→6)-3-O-benzyl-β -D-galactopyranoside (Compound 10)

To a solution of Compound 4 (700 mg, 1.89 mmol) and Compound 1A (1.67 g, 3.20 mmol) dissolved in acetonitrile (15 ml) was added Molecular Sieves 3A (2.3 g) and the solution was stirred at room temperature for 5 hrs. To the solution cooled to −40° C. were added N-iodosuccinimide (1.44 g, 6.40 mmol) and further trifluoromethanesulfonic acid (56.8 μl, 0.64 mmol) and a mixture was stirred at the same temperature for 2 hrs. After a completion of the reaction was confirmed by thin layer chromatography, the reaction solution was neutralized with triethylamine, the molecular sieves was filtered off and the filtrate was concentrated under reduced pressure. The resulting residue was extracted with chloroform, washed with successive $Na_2CO_3$, 2N-HCl and Na$_2$S$_2$O$_3$ and dried over Na$_2$SO$_4$, and the solvent was distilled off. The resultant syrup was subjected to column chromatography (Wakogel; C-200) and a syrup Compound 9 (810 mg, 50.9%) and Compound 10 (417 mg, 26.2%) were obtained from a fraction eluting with 25/1 toluene/MeOH.

EXAMPLE 5

2-(Trimethylsilyl)ethyl O-(methyl 5-acetamido-4,7,8,9-tetra-O-acetyl-3,5-dideoxy-D-glycero-α-D-galacto-2-nonulopyranosylonate)-(2→6)-3-O-benzyl-β-D-galactopyranoside (Compound 9)

and 2-(Trimethylsilyl)ethyl O-(methyl 5-acetamido-4,7,8,9-tetra-O-acetyl-3,5-dideoxy-D-glycero-β-D-galacto-2-nonulopyranosylonate)-(2→6)-3-O-benzyl-β-D-galactopyranoside (Compound 10)

To a solution of Compound 4 (700 mg, 1.89 mmol) and Compound 1A (1.67 g, 3.20 mmol) dissolved in dichloromethane (15 ml) was added Molecular Sieves 3A (2.3 g) and the solution was stirred at room temperature for 5 hrs. To the solution cooled to −20° C. were added N-iodosuccinimide (1.44 g, 6.40 mmol) and further trifluoromethanesulfonic acid (56.8 μl, 0.64 mmol) and a mixture was stirred at the same temperature for 2 hrs. After a completion of the reaction was confirmed by thin layer chromatography, the reaction solution was neutralized with triethylamine, the molecular sieves was filtered off and the filtrate was concentrated under reduced pressure. The resulting residue was extracted with chloroform, washed with successive Na$_2$CO$_3$, 2N-HCl and Na$_2$S$_2$O$_3$, and dried over Na$_2$SO$_4$ and the solvent was distilled off. The resultant syrup was subjected to silica gel column chromatography (Wakogel; C-200) and a syrup Compound 9 (513 mg, 32.2%) and Compound 10 (791 mg, 49.7%) were obtained from a fraction eluting with 25/1 toluene/MeOH.

The optical rotation and nuclear magnetic resonance data of Compound 10 are shown below.

$[\alpha]_D$ −10.44° (c 0.8 Chloroform); $^1$H NMR(CDCl$_3$) Gal unit δ0.98(m 2H, Me$_3$SiCH$_2$CH$_2$O), 2.41(d, 1H, J=1.8 Hz, 4-OH), 3.21(d, 1H, J=2.9 Hz, 2-OH), 4.22(d, 1H, J$_{1,2}$=7.7 Hz, H-1), 7.35-7.50(m, 5H, ph); Neu 5Ac unit δ1.84(S, 3H, AcN), 2.00, 2.02, 2.05, 2.12 (4s, 12H, 4AcO), 2.45(dd, 1H, J$_{3a,3e}$=12.8 Hz, J$_{3e,4}$=4.9 Hz, H-3e), 3.79(s, 3H, COOMe), 3.93(ddd, 1H, J$_{5,6}$=10.5 Hz, J$_{5,NH}$=9.5 Hz, H-5), 4.17(dd, 1H, J$_{9,9'}$=12.6 Hz, H-9), 4.37(dd, 1H, J$_{6,7}$=2.1 Hz, H-6), 4.74(dd, 1H, J$_{8,9'}$=2.2 Hz, H-9'), 5.27 5.42(m, 3H, H-4,7,8), 5.73(d, 1H, NH)

EXAMPLE 6

2-(Trimethylsilyl)ethyl O-(methyl 5-acetamido-4,7,8,9-tetra-O-acetyl-3,5-dideoxy-D-glycero-α-D-galacto-2-nonulopyranosylonate)-(2→3)-(2,6-di-O-benzyl-β-D-galactopyranosyl)-(1→4)-2,3,6-tri-O-benzyl-β-D-glucopyranoside (Compound 11)

and 2-(Trimethylsilyl)ethyl O-(methyl 5-acetamido-4,7,8,9-tetra-O-acetyl-3,5-dideoxy-D-glycero-β-D-galacto-2-nonulopyranosylonate)-(2→3)-(2,6-di-O-benzyl-β-D-galactopyranosyl)-(1→4)-2,3,6-tri-O-benzyl-β-D-glucopyranoside (Compound 12)

To a solution of Compound 1A (1.42 g, 2.49 mmol) and Compound 5 (1.00 g, 1.25 mmol) dissolved in acetonitrile was added Molecular Sieves 3A (3 g) and the solution was stirred at room temperature for 5 hrs. To the solution cooled to −35° C. were added N-iodosuccinimide (1.12 g, 4.98 mmol) and further trifluoromethanesulfonic acid (44 μl, 0.43 mmol) and a mixture was stirred at the same temperature for 2 hrs. After a completion of the reaction was confirmed by thin layer chromatography, triethylamine was added to the reaction solution until it was made neutral and the reaction solution was filtered with celite. The filtrate and the washings were combined and extracted with dichloromethane. The dichloromethane layer was washed with successive 2N-HCl, Na$_2$CO$_3$, Na$_2$S$_2$O$_3$ and H$_2$O, and dehydrated with Na$_2$SO$_4$ and concentrated under reduced pressure. The resultant syrup was subjected to column chromatography (silica gel-OG-II) and from the eluate (1.5% MeOH in toluene) were Compound 11 (978 mg, 59%) and Compound 12 (201 mg, 12%).

The optical rotation and NMR data of Compounds 11 and 12 are shown below.

Compound 11: $[\alpha]_D$+4.3°; $^1$H NMR(CDCl$_3$) Lac unit δ1.00(m, 2H, Me$_3$S iCH$_2$CH$_2$), 7.18-7.38(m, 25H, 5Ph); Neu 5Ac unit δ1.85(s, 3H, AcN), 1.8 7, 1.96, 1.99, 2.07(4s, 12H, 4AcO), 2.48(dd, 1H, J$_{gem}$=13.0 Hz, J$_{3a,4}$=4.8 Hz, H-3e), 3.83(s, 3H, MeO), 4.86(m, 1H, H-4), 5.25(d, 1H, J$_{5,NH}$=7.2 Hz, NH), 5.28(dd, 1H, J$_{6,7}$=1.6 Hz, J$_{7,8}$=7.0 Hz, H-7) and 5.36(ddd, 1H, H-8)

Compound 12: $[\alpha]_D$−4.7°; $^1$H NMR(CDCl$_3$) Lac unit δ1.03(m, 2H, Me$_3$S iCH$_2$CH$_2$), 7.19-7.37(m, 25H, 5Ph); Neu 5Ac unit δ1.72(s, 3H, AcN), 1. 94, 1.96, 2.07, 2.08(4s, 12H, 4AcO), 2.53(dd, 1H, J$_{gem}$=13.3 Hz, J$_{3e,4}$=4.6 Hz, H-3e), 3.60(s, 3H, MeO), 5.16(m, 1H, H-4), 5.18(dd, 1H, H-7) and 5. 26(m, 1H, H-8)

What is claimed is:

1. A process of preparing an O-glycosyl compound of sialic acid which comprises reacting a 2-thioglycoside of sialic acid with a galactose or a lactose in the presence of N-iodosuccinimide and trifluoromethanesulfonic acid, in acetonitrile or dichloromethane under substantially anhydrous conditions between −80° and −20° C.

2. A process of claim 1 wherein the thioglycoside of sialic acid is methyl(methyl 5-acetamido-4,7,8,9-tetra-O-acetyl-3,5-dideoxy- 2-thio-D-glycero-D-galacto-2-nonulopyranosid)onate or methyl(phenyl 5-acetamido-4,7,8,9-tetra-O-acetyl-3,5-dideoxy-2-thio-D-glycero-D-galacto-2-nonulopyranosid)onate.

3. A process of claim 1 wherein the sugar is a galactose selected from the group consisting of 2-(trimethylsilyl)ethyl 6-O-benzoyl-β-D-galactopyranoside, 2-(trimethylsilyl)ethyl 3-O-benzoyl-β-D-galactopyranoside and 2-(trimethylsilyl)ethyl 3-O-benzoyl-β-D-galactopyranoside.

4. A process of claim 1 wherein the sugar is 2-(trimethylsilyl)ethyl O-(2,6-di-O-benzyl-β-D-galactopyranosyl)-(1→4)-2,3,6-tri-O-benzyl-β-D-glucopyranoside.

5. A process of claim 1 wherein methyl(methyl 5-acetamido-4,7,8,9-tetra-O-acetyl-3,5-dideoxy-2-thio-D-glycero -D-galacto-2-nonulopyranosid)onate is reacted with 2-(trimethylsilyl)ethyl 6-O-benzoyl-β-D-galactopyranoside.

6. A process of claim 1 wherein methyl(phenyl 5-acetamido-4,7,8,9,-tetra-O-acetyl-3,5-dideoxy-2-thio-D-glycero-D-galacto-2-nonulopyranosid)onate is reacted with 2-(trimethylsilyl)ethyl 6-O-benzoyl-β-D-galactopyranoside.

7. A process of claim 1 wherein methyl(methyl 5-acetamido-4,7,8,9-tetra-O-acetyl-3,5-dideoxy-2-thio-D-glycero-D-galacto-2-nonulopyranosid)onate is reacted with 2-(trimethylsilyl)ethyl 3-O-benzoyl-$\beta$-D-galactopyranoside.

8. A process of claim 1 wherein methyl(phenyl 5-acetamido-4,7,8,9-tetra-O-acetyl-3,5-dideoxy-2-thio-D-glycero-D-galacto-2-nonulopyranosid)onate is reacted with 2-(trimethylsilyl)ethyl 3-O-benzyl-$\beta$-D-galactopyranoside.

9. A process of claim 1 wherein methyl(phenyl 5-acetamido-4,7,8,9-tetra-O-acetyl-3,5-dideoxy-2-thio-D-glycero-D-galacto-2-nonulopyranosid)onate is reacted with 2-(trimethylsilyl)ethyl O-(2,6-di-O-benzyl-$\beta$-D-galactopyranosyl)-(1→4)-2,3,6-tri-O-benzyl-$\beta$-D-glucopyranoside.

* * * * *

UNITED STATES PATENT AND TRADEMARK OFFICE
CERTIFICATE OF CORRECTION

PATENT NO.  : 5,371,202
DATED       : December 6, 1994
INVENTOR(S) : Akira HASEGAWA It is certified that error appears in the above-indentified patent and that said Letters Patent is hereby corrected as shown below:

On the title page, Item [73], the Assignee should read:

--The Nisshin Oil Mills, Ltd., Tokyo, JAPAN

Signed and Sealed this

Twenty-second Day of August, 1995

*Attest:*

BRUCE LEHMAN

*Attesting Officer*            *Commissioner of Patents and Trademarks*